United States Patent [19]

Jouffret

[11] 3,978,141

[45] Aug. 31, 1976

[54] PROCESS FOR SPLITTING ALKYLAROMATIC HYDROPEROXIDES INTO PHENOLIC COMPOUNDS

[75] Inventor: Michel Jouffret, Francheville-le-Bas, France

[73] Assignee: Rhone-Poulenc S.A., Paris, France

[22] Filed: Aug. 28, 1974

[21] Appl. No.: 501,434

[30] Foreign Application Priority Data

Aug. 31, 1973 France .................................. 73.1525

[52] U.S. Cl. .......................... 260/621 C; 260/610 B; 260/613 R; 260/624 R
[51] Int. Cl.² ........................................ C07C 39/06
[58] Field of Search ............ 260/621 C, 586, 624 R, 260/610 B, 613 R

[56] References Cited
UNITED STATES PATENTS

| 3,187,052 | 6/1965 | Nelson et al. ......................... 260/593 |
| 3,798,277 | 3/1974 | Masatoshi et al. ................ 260/621 C |

FOREIGN PATENTS OR APPLICATIONS

| 484,329 | 6/1952 | Canada ............................. 260/621 C |
| 42-2342 | 2/1967 | Japan ............................... 260/621 C |

*Primary Examiner*—James O. Thomas, Jr.
*Assistant Examiner*—W. B. Lone
*Attorney, Agent, or Firm*—Cushman, Darby & Cushman

[57] ABSTRACT

Process for splitting primary alkylaromatic hydroperoxides to yield phenolic products is described which consists of reacting the hydroperoxide with a catalytic amount of a compound with an acid reaction, in an organic solvent medium, the characteristic feature being that the splitting medium is a mixture consisting of:

a. at least one solvent chosen from the group of aprotic polar solvents formed by polymethylene-sulphones, alkylene glycol carbonates which contain 2 to 4 carbon atoms (in the alkylene portion) and aliphatic or aromatic nitriles, and
b. at least one hydroxylic solvent taken from the group formed by aliphatic alcohols containing 1 to 3 carbon atoms and alkylene glycols containing up to 4 carbon atoms.

10 Claims, No Drawings

PROCESS FOR SPLITTING ALKYLAROMATIC HYDROPEROXIDES INTO PHENOLIC COMPOUNDS

The present invention relates to a process for splitting certain alkylaromatic hydroperoxides, by means of compounds with an acid reaction, to form phenolic products.

Various methods can be applied to decompose alkylaromatic hydroperoxides. One method consists of using aqueous sulphuric acid of concentration between 20 and 65% by weight, in varying proportions, the hydroperoxide being employed either in the pure state or dissolved in an organic solvent which can be, for example, the hydrocarbon in which and from which it was prepared by oxidation. In another method, a catalytic amount of concentrated sulphuric acid is used in the presence of a suitable solvent such as methanol.

In some cases, the acid splitting reaction does not take place very readily and it is found that the selectivity with respect to phenolic products is inadequate, and this is an obstacle to the industrial application of such processes. For example, in the case of p-xylyl hydroperoxide, the splitting reaction, carried out in the presence of concentrated sulphuric acid in methanol, 2.69% by weight of acid being used relative to the hydroperoxide, takes place according to two reaction schemes, one of which leads to p-cresol and the other to p-tolualdehyde, with respective yields, relative to the hydroperoxide decomposed, of 55% and 25% (see E. J. LORAND et al., J. Am. Chem. Soc. 77, 4035 (1955).

A process for splitting primary alkylaromatic hydroperoxides has now been found and it is this which forms the subject of the present invention. According to the present invention there is provided a process which comprises reacting the hydroperoxide with a catalytic amount of a compound with an acid reaction in an organic solvent medium, this medium comprising:
a. at least one aprotic polar solvent which is a polymethylene-sulphone or an alkylene glycol carbonate which contains 2 to 4 carbon atoms in the alkylene portion or an aliphatic or aromatic nitrile, and
b. at least one hydroxylic solvent which is an aliphatic alcohol containing 1 to 3 carbon atoms or an alkylene glycol containing 2 to 4 carbon atoms.

This invention specifically relates to the acid splitting of primary alkylaromatic hydroperoxides which generally have the formula:

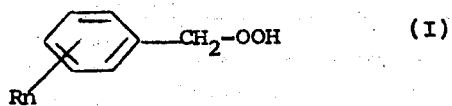

(I)

in which:

R represents an alkyl radical containing 1 to 4 carbon atoms or an alkoxy radical containing 1 to 4 carbon atoms, and $n$ is equal to 1, 2, or 3; with the proviso that the radical R (when $n$ is equal to 1) or at least one of the radicals R (when $n$ is greater than 1) is situated in the ortho- or para-position relative to the hydroperoxymethylene group.

R may, for example, represent a methyl, ethyl, isopropyl, methoxy, ethoxy or isopropoxy radical, methyl and methoxy being especially preferred.

Specific examples of alkylaromatic hydroperoxides which can be reacted by the process of the present invention include o-xylyl hydroperoxide, p-xylyl hydroperoxide, 2,4-dimethyl-benzyl hydroperoxide, 3,4-dimethyl-benzyl hydroperoxide, 2,4,5-trimethyl-benzyl hydroperoxide, 2,4,6-trimethyl-benzyl hydroperoxide and p-methoxy-benzyl hydroperoxide. The splitting process according to this invention is particularly appropriate for o-xylyl hydroperoxide and p-xylyl hydroperoxide.

The primary hydroperoxides of the present invention are known and can be prepared in accordance with the usual processes, for example by passing a gas containing oxygen, under non-catalytic conditions, in the liquid phase, through the corresponding hydrocarbon heated to the appropriate temperature; the hydroperoxides obtained can be purified in accordance with conventional methods, such as conversion to the sodium salt and treatment with carbon dioxide.

Suitable polymethylene-sulphones include those which contain 3 to 6 methylene groups, it being possible for one or more of these methylene groups optionally to be substituted by an alkyl radical with 1 to 4 carbon atoms, for example methyl, ethyl, propyl and butyl radicals.

Specific examples of such sulphones include trimethylene-sulphone, $\alpha$-methyltrimethylene-sulphone, $\alpha$-methyltetramethylene-sulphone, tetramethylene-sulphone (sulpholane), pentamethylene-sulphone, $\alpha$-methylpentamethylene-sulphone, hexamethylene-sulphone and $\alpha,\alpha'$-dimethyltetramethylene-sulphone. Preferred polymethylene-sulphones are sulpholane, which is especially preferred, and its alkyl-substituted derivatives, such as those described in French Pat. No. 1,342,449.

Suitable glycol carbonates include ethylene glycol carbonate, propylene glycol carbonate and butane-2,3-diol carbonate.

Suitable nitriles include acetonitrile, propionitrile and benzonitrile.

The simultaneous use of these aprotic polar solvents and these hydroxylic solvents (such as alcohols or alkylene glycols) makes it possible, unexpectedly, to effect the splitting of the primary hydroperoxides, in the presence of catalytic amounts of a compound with an acid reaction, with a selectivity in relation to phenolic products which is very much greater than that obtained by known processes, thus providing improved yields of the desired products.

The hydroxylic solvents which are suitable for carrying out the process of the present invention include methyl alcohol, ethyl alcohol, propyl alcohol and isopropyl alcohol, ethylene glycol, propane-1,2-diol and butane-1,4-diol.

It is, of course, possible to use a mixture of two or more aprotic solvents with one or more hydroxylic solvents. Mixtures of sulpholane and acetonitrile with methanol or ethylene glycol are particularly suitable.

In practice, the process of this invention can be carried out by introducing the hydroperoxide in the pure state into a mixture consisting of the compound with an acid reaction and the chosen aprotic polar solvent together with one of the specified alcohols or alkylene glycols, heated beforehand to 20°C, to the reflux temperature of the mixture, preferably to from 50° to 110°C. The hydroperoxide can also very successfully be introduced into the above mixture in the form of a solution in one and/or the other of the chosen solvents.

It is not however necessary to use a rigorously pure hydroperoxide; it is possible to use the crude product resulting from the partial oxidation of the hydrocarbon, after having freed it from the greater part of the excess unconverted hydrocarbon, for example by distillation.

The acid agent used can be an inorganic or organic protonic acid, such as those used heretofore, especially strong acids. Particularly suitable acids include hydrochloric acid, nitric acid, sulphuric acid, alkanesulphonic acids such as methanesulphonic acid, and arylsulphonic acids such as benzenesulphonic and para-toluenesulphonic acids. The acid is preferably used in the form of the pure acid or concentrated aqueous solution. Although protonic acids are preferred, it is also possible to use acid catalysts such as anhydrous ferric chloride, boron trichloride, silica, diatomaceous earth, and Friedel-Crafts catalysts such as aluminium chloride and zinc chloride.

The amount of pure acid agent employed in order to split the hydroperoxides can vary within fairly wide limits; it has been found that amounts from 0.1% to 40% by weight, based on the weight of the hydroperoxide employed, are generally sufficient to effect the splitting reaction rapidly.

The concentration of the hydroperoxide employed in the solvent mixture is not critical and can vary within wide limits. Thus it can be, for example, from 1 to 50% by weight.

The composition of the solvent mixture is preferably such that it contains 40 to 98% by weight of aprotic polar solvent and 60 to 2% by weight of hydroxylic solvent, especially 60 to 96% by weight of polar solvent and 40 to 4% by weight of hydroxylic solvent.

Although the molar ratio of hydroxylic solvent to hydroperoxide can vary within wide limits, an amount of hydroxylic solvent which introduces at least one alcohol group per mol of hydroperoxide is preferably used.

When the introduction of the hydroperoxide is complete, the reaction is allowed to continue, at the desired temperature, for the period of time necessary to achieve a conversion of the hydroperoxide which is as complete as possible, with the minimum amount of degradation reactions. The reaction mixture can then, where appropriate, be neutralised by a base.

When a protonic acid is used, the small amount which is necessary is completely soluble in the medium, so that the reaction mixture is perfectly homogeneous and only moderate stirring is required in order to bring the reagents into contact. Furthermore, when the reaction mixture is neutralised, the amount of basic agent necessary is very low; as a consequence only small amounts of the corresponding salts are formed, which are partially dissolved in the medium, so that it is possible to dispense with an additional separation step.

The residual solution can be treated in a suitable manner in order to isolate the desired phenolic and carbonyl products from it, for example by fractional distillation. If so desired, it is possible to work under temperature and pressure conditions such that the carbonyl derivative is removed as it is formed.

The following Examples further illustrate the present invention.

EXAMPLES 1 to 5

12.5 g. of a mixture of sulpholane and the chosen hydroxylic solvent, the percentage composition by weight and nature of which varies: 95% sulpholane and 5% methanol (Example 1), 90% sulpholane and 10% methanol (Example 2), 80% sulpholane and 20% methanol (Example 3), 50% sulpholane and 50% methanol (Example 4) and 90% sulpholane and 10% ethylene glycol (Example 5), and the chosen catalytic amount of an aqueous solution of 98% by weight pure sulphuric acid are introduced into a glass flask which is equipped with a central stirrer, a reflux condenser, a dropping funnel and a thermometer and which is heated externally.

The reaction mixture is heated to 60°C, and then 2.82 g. of p-xylyl hydroperoxide containing 61.5% by weight of pure hydroperoxide (Examples 1 to 4) and 2.62 g. of p-xylyl hydroperoxide containing 66% by weight of pure hydroperoxide (Example 5) are introduced rapidly.

When the addition is complete, the reaction mixture is stirred at the chosen temperature for a definite period of time until deperoxidation has stopped.

Heating is then stopped and the strong acid employed is neutralised by means of the theoretical amount of a normal solution of sodium hydroxide in methanol.

The yields of p-cresol, p-tolualdehyde, the methylketal of p-tolualdehyde and p-methyl-benzyl alcohol relative to the hydroperoxide consumed are measured by vapour phase chromatographic analyses.

The following Table gives the results obtained:

| EXAMPLES | 1 | 2 | 3 | 4 | 5 |
|---|---|---|---|---|---|
| Mixture of solvents: percentage composition by weight | Sulpholane 95% Methanol 5% | Sulpholane 90% Methanol 10% | Sulpholane 80% Methanol 20% | Sulpholane 50% Methanol 50% | Sulpholane 90% Ethylen glycol 10% |
| Mixture: grams | 12.5 | 12.5 | 12.5 | 12.5 | 12.5 |
| Pure p-xylyl hydroperoxide, mol | 0.0125 | 0.0125 | 0.0125 | 0.0125 | 0.0125 |
| Pure $H_2SO_4$, mol | 0.0025 | 0.0025 | 0.0025 | 0.005 | 0.0025 |
| % $H_2SO_4$/hydroperoxide, by weight | 14.16% | 14.16% | 14.16% | 28.32% | 14.16% |
| Temperature °C | 60° | 60° | 60° | 60° | 60° |
| Duration | 12 minutes | 30 minutes | 2 hours | 1 hour 45 mins. | 9 minutes |
| % residual peroxide oxygen | 11% | 4% | 2.6% | 10.6% | 26% |
| Yield of p-cresol | 70.2% | 85% | 73% | 64.7% | 72.8% |
| Yield of p-tolualdehyde | 11.3% | 6.5% | 9.54% | 18.8% | 6% |
| the methylketal of p-tolualdehyde | 5% | 6.5% | 4% | 5.7% | — |
| p-methyl-benzyl alcohol | 7.45% | — | 4.3% | 7.6% | 8.6% |

Preparation of p-xylyl hydroperoxide

The oxidation of p-xylene is carried out at 175°C., in a stainless steel autoclave, under a total pressure of 20 bars, with a flow rate of 320 liters per hour of air containing 8% of oxygen, per kilogram of p-xylene (measured under normal temperature and pressure).

After 50 minutes under these conditions, the mixture is cooled and is transferred to a boiler; the unconverted p-xylene is then removed by distillation under reduced pressure without exceeding 40°C., in the boiler. An oxidised product containing 61% to 66% by weight of p-xylyl hydroperoxide is thus obtained.

EXAMPLES 6 and 7

12.5 g. of a mixture of sulpholane (90% by weight) and methanol (10% by weight; Example 6), or of acetonitrile (90%) and methanol (10%; Example 7), and the chosen catalytic amount of an aqueous solution of 98% by weight pure sulphuric acid are introduced into a glass flask which is equipped as in Example 1 and is heated externally.

The reaction mixture is heated to 60°C, and then 2.68 g. of o-xylyl hydroperoxide containing 64.5% by weight of pure hydroperoxide are introduced rapidly.

Once the addition is complete, the reaction mixture is stirred at the chosen temperature for a definite period of time until deperoxidation has stopped. The procedure of Example 1 is followed thereafter.

The yields of o-cresol, o-tolualdehyde and the methylketal of o-tolualdehyde, relative to the hydroperoxide consumed, are measured by vapour phase chromatographic analyses.

The following Table gives the results obtained:

| EXAMPLE | 6 | 7 |
| --- | --- | --- |
| Mixture of solvents: percentage composition by weight | Sulpholane 90% Methanol 10% | Acetonitrile 90% Methanol 10% |
| Mixture: grams | 12.5 | 12.5 |
| Pure o-xylyl hydroperoxide, mol | 0.0125 | 0.0125 |
| Pure $H_2SO_4$, mol | 0.0025 | 0.0025 |
| % $H_2SO_4$/hydroperoxide, by weight | 14.16% | 14.16% |
| Temprature °C. | 60° | 60° |
| Duration | 25 minutes | 1 hour 30 mns. |
| % residual peroxide oxygen | 5.6% | 4% |
| Yield of o-cresol | 73% | 65% |
| Yields of o-tolualdehyde | 3% | 3.5% |
| the methylketal of o-tolualdehyde | 1.5% | 1% |
| o-methyl-benzyl alcohol | — | — |

Preparation of o-xylyl hydroperoxide o-Xylene is oxidised in a manner identical to that described in Example 1 for p-xylene. The purity of the hydroperoxide obtained is comparable to that of p-xylyl hydroperoxide.

I claim:

1. In a process for the deperoxidization of a primary alkylaromatic hydroperoxide of the general formula:

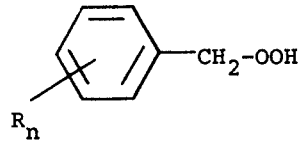

in which:

R represents an alkyl radical containing 1 to 4 carbon atoms and $n$ represents an integer from 1 to 3, with the proviso that when $n$ is equal to 1 the radical R, or when $n$ is greater than 1 at least one of the radicals R, is in the ortho or para-position relative to the hydroperoxymethylene group, to form phenolic compounds which comprises reacting the hydroperoxide with 0.1 to 40% by weight of a compound possessing an acid reaction selected from the group consisting of inorganic and organic protonic acids, Friedel-Crafts catalysts, silica, and diatomaceous earth acid catalysts at a temperature from 20°C to 110°C in the presence of an inert organic solvent, the improvement wherein said solvent comprises:
  a. 40 to 98% by weight of at least one aprotic polar solvent selected from the group consisting (1) polymethylene-sulphones, (2) alkylene glycol carbonates which contain 2 to 4 carbon atoms in the alkylene portion and (3) acetonitrile, propionitrile and benzonitrile and
  b. 60 to 2% by weight of at least one hydroxylic solvent selected from the group consisting of alkanols containing 1 to 3 carbon atoms and alkylene glycols containing 2 to 4 carbon atoms, whereby the selectivity of the deperoxidization is increased with respect to the phenolic compounds.

2. Process according to claim 1, in which R is a methyl radical.

3. Process according to claim 2, in which the hydroperoxide is o-xylyl hydroperoxide or p-xylyl hydroperoxide.

4. Process according to claim 1 in which the polymethylene-sulphone contains 3 to 6 methylene groups, one or more of said methylene groups optionally being substituted by an alkyl radical with 1 to 4 carbon atoms.

5. Process according to claim 1 in which the aprotic polar solvent is selected from sulpholane, ethylene glycol carbonate, propylene glycol carbonate, acetonitrile and propionitrile.

6. Process according to claim 1 in which the hydroxylic compound is selected from methyl alcohol, ethyl alcohol, ethylene glycol and propane-1,2-diol.

7. Process according to claim 1 which is carried out at 50° to 110°C.

8. Process according to claim 1 in which the solvent medium contains 60 to 96% of the aprotic polar solvent and 40 to 4% of the hydroxylic solvent.

9. Process according to claim 1 in which the hydroxylic solvent is present in an amount such that at least one OH group is present per mol of hydroperoxide.

10. In a process for the deperoxidization of xylyl hydroperoxide to form cresols, which comprises reacting the hydroperoxide with 0.1 to 40% by weight of a protonic acid selected from hydrochloric acid, nitric acid, sulphuric acid, methanesulphonic acid, benzenesulphonic acid or para-toluenesulphonic acid in the presence of an inert organic solvent, the improvement wherein the deperoxidization is carried out at 50° – 110°C in the presence of a mixture of a) 40 to 98 percent by weight of sulpholane or acetonitrile and b) 60 to 2 percent by weight of methanol, whereby the selectivity of the deperoxidization is increased with respect to cresol.

* * * * *

UNITED STATES PATENT OFFICE
CERTIFICATE OF CORRECTION

Patent No. 3,978,141     Dated August 31, 1976

Inventor(s) Michel Jouffret

It is certified that error appears in the above-identified patent and that said Letters Patent are hereby corrected as shown below:

Foreign Application Priority Data should read

--Aug. 31, 1973    France     73,31525--

Signed and Sealed this

*First* Day of *November 1977*

[SEAL]

Attest:

RUTH C. MASON      LUTRELLE F. PARKER
*Attesting Officer*     *Acting Commissioner of Patents and Trademarks*